United States Patent [19]

Castile

[11] Patent Number: 5,513,647

[45] Date of Patent: May 7, 1996

[54] METHOD FOR MEASURING ADULT-TYPE PULMONARY FUNCTION TESTS IN SEDATED INFANTS AND APPARATUS THEREFOR

[76] Inventor: Robert G. Castile, 1063 Cannonade Ct., Gahanna, Ohio 43230

[21] Appl. No.: 237,125

[22] Filed: May 3, 1994

[51] Int. Cl.⁶ .............................. A61H 31/02; A61B 5/085
[52] U.S. Cl. ............... 128/720; 128/204.18; 128/204.21; 128/204.23; 128/205.26
[58] Field of Search ................................. 128/671, 716, 128/720, 725, 727, 728, 730, 717, 718, 719, 721–724, 726, 729, 200.24, 204.18, 204.21, 204.23, 205.26; 601/41–45

[56] References Cited

U.S. PATENT DOCUMENTS

| | | |
|---|---|---|
| 1,055,267 | 3/1913 | Gibson . |
| 2,490,395 | 12/1949 | Wilm . |
| 2,833,275 | 5/1958 | Tunnicliffe . |
| 2,869,537 | 1/1959 | Chu . |
| 3,042,024 | 7/1962 | Mendelson . |
| 3,043,292 | 7/1962 | Mendelson . |
| 3,481,327 | 12/1969 | Drennen . |
| 3,509,899 | 5/1970 | Hewson ................................. 601/41 |
| 3,621,835 | 11/1971 | Suzuki et al. ......................... 128/725 |
| 3,786,809 | 1/1974 | Kitrilakis ............................... 128/191 |
| 4,004,579 | 1/1977 | Dedo ...................................... 128/28 |
| 4,539,984 | 9/1985 | Kiszel et al. ...................... 128/204.23 |
| 4,977,889 | 12/1990 | Budd ...................................... 601/44 |
| 5,222,478 | 6/1993 | Scarberry et al. . |
| 5,261,397 | 12/1993 | Grunstein .......................... 128/204.18 |
| 5,318,038 | 6/1994 | Jackson et al. ....................... 128/716 |

OTHER PUBLICATIONS

Turner, D. J., et al., "Assessment of Forced Expiratory Volume—Time Parameters in Decting Histamine–induced Bronchoconstriction in Wheezy Infants", Pediatric Pulmonology 15: pp. 220–224 (1993).

Turner, D. J., et al., "Assessment of Respiratory Function in Infants Pumped to Higher Lung Volumes", Am. Rev. of Respiratory Disease 143: p. 126 (abstract) (1991).

Primary Examiner—Angela D. Sykes
Assistant Examiner—Stephen D. Huang
Attorney, Agent, or Firm—Vorys, Sater, Seymour & Pease

[57] ABSTRACT

A maximum expiratory vital capacity maneuver is produced in an infant by a method which comprises the steps of 1) inflating the lungs of an infant with air synchronously with natural tidal inspiration to a lung volume greater than that reached at end-tidal inspiration for a number of respiratory cycles until the infant's natural tidal breathing pauses;

2) during the pause in breathing, rapidly inflating the infant's lungs to substantially total lung volume;

3) immediately compressing the chest and abdomen of said infant to produce a maximum forced expiration.

The data generated by measuring flow rates and volumes during this maneuver can be used to derive the conventional measurements of pulmonary function for such infants and provide an opportunity to compare those measurements with the corresponding measurements obtained for adults and older children who are capable of performing the maneuver voluntarily under instructions.

The invention also encompasses an apparatus for performing maximum forced expiration in infants under automatic control.

17 Claims, 3 Drawing Sheets

METHOD FOR MEASURING ADULT-TYPE PULMONARY FUNCTION TESTS IN SEDATED INFANTS AND APPARATUS THEREFOR

BACKGROUND OF THE INVENTION

1. Field of the Invention

This invention relates to measurement of pulmonary function in infants and more particularly to producing forced expiratory maneuvers in infants over the entire vital capacity range.

2. Brief Description of the Prior Art

Assessment of pulmonary function is of fundamental importance in the diagnosis and treatment of diseases involving the lung. One of the simplest and yet most useful tests of pulmonary function is the forced expiration. In this test the patient makes a maximum inspiration, filling the lungs to their maximum volume, and immediately expels the inhaled air as rapidly as possible to empty the lungs to the minimum volume attainable by this maneuver. Measurement of the volume rate of expiration and the total amount of air expired over the time of the forced expiration yields a number of parameters that can be used as measures of pulmonary function. Plots of exhaled volume versus time are generated and various measures are derived from the plotted curves. Particularly useful diagnostic data derived from the forced maximum expiratory flow plot are the forced expiratory flow in the first second of the forced expiration ($FEV_1$), the expiratory flow rate averaged over the period from a volume of 25% to 75% of the total expired air volume ($FEV_{25-75}$), and the plot of the flow rate versus volume of expired air, defined as the maximum expiratory flow-volume curve (MEFVC). The data from a maximum forced flow maneuver can also be used in combination with measurements of thoracic gas volume, e.g., obtained using a full-body plethysmograph, nitrogen washout or helium dilution, to determine the proportions of that volume that can and cannot be exchanged by the patient. Such divisions of the total lung capacity (TLC) are generally referred to as fractional lung volumes (FLV). These tests are useful for quantitating levels of dysfunction occurring in relation to both obstructive and restrictive pulmonary processes.

One clinically important application of pulmonary function measurements is found in the evaluation of lung condition and function in adults and older children having cystic fibrosis (CF), wherein maximum expiratory flow-volume curves (MEFVCs) and the fractional lung volumes (FLVs) play a central role. Typically, the presence of obstructive lung disease accompanying cystic fibrosis can be diagnosed by the lower rates of expiratory flow that the patient can produce with maximum effort. When adults and older children having cystic fibrosis are admitted to a hospital for treatment of pulmonary exacerbations with intravenous antibiotics and intensive chest physical therapy, MEFVCs and FLVs are routinely used to monitor changes in lung function from the time of hospital admission to discharge after conclusion of the treatment regimen.

However, infants, i.e., typically those under about two years of age, cannot voluntarily perform the forced expiratory maneuver that is needed to measure forced expiratory flows and to derive measures of fractional lung volumes useful in diagnosis. Hitherto, pulmonary function measurements have been available only for the tidal breathing range in such patients. Such data has some clinical utility, but is not comparable to the data obtained by forced expiratory maneuvers in older patients.

Attempts have been made to obtain forced expiratory volume versus time curves for infants by using mechanical compression of the thorax and abdomen with an inflatable vest or similar mechanical compression device. Such techniques have mostly been limited to forced compression from a condition of end-tidal inspiration. Attempts to extend measurements of respiratory mechanics in infants beyond the tidal breathing range have been limited by the inability to disengage infants from their obligatory tidal respiratory cycle. Recently, Turner, et al., *Pediatric Pulmonology* 15, 220–224 (1993) have reported a technique that permits rapid thoracic compression (RTC) from an increased lung volume. According to Turner at al., the lung volume of the infants was raised by inflating the infants during tidal inspiration by administering additional air through a face mask at a pressure of about 15 cm $H_2O$. An inflatable device was utilized to compress the thorax and abdomen immediately after this enhanced inspiration, while the expired flow and volume were measured as a function of time. However, in this maneuver the infants were not inflated to near TLC and terminated the forced expiratory maneuver prematurely by actively inspiring, even during chest compression. Consequently, although Turner's technique represents an advance over the previous procedures, it still does not permit a forced expiratory maneuver in infants that is similar to the voluntary maneuvers performed by adults and older children, in that it does not permit the generation of forced flows over the entire vital capacity (VC) range.

It is known that infants occasionally pause for a few seconds in their normal tidal respiration, generally after taking a deep breath and exhaling in a kind of sigh. Furthermore, it is known that such a pause can be induced by forcibly enhancing an infant's normal tidal respiration by inflating the infant's lungs synchronously with natural inspiration to a volume greater than normal end-tidal inspiration for a few breaths. However, it has not been known to utilize this induced pause for performing a maximum forced expiratory maneuver in infants.

Accordingly, a need has continued to exist for a method of performing forced expiratory flow maneuvers in infants from lung volumes approaching total lung capacity and extending to residual volume (RV) with flow limitation occurring over most of the VC range.

SUMMARY OF THE INVENTION

This problem has now been solved by a method of producing a maximum expiratory vital capacity maneuver in an infant which comprises the steps of 1) inflating the lungs of an infant with air synchronously with natural tidal inspiration to a lung volume greater than that reached at end-tidal inspiration for a number of respiratory cycles until the infant's natural tidal breathing pauses;

2) during the pause in breathing, rapidly inflating the infant's lungs to substantially total lung volume;

3) immediately compressing the chest and abdomen of said infant to produce a maximum forced expiration.

The data generated by measuring flow rates and volumes during this maneuver can be used to derive the conventional measurements of pulmonary function for such infants and provide an opportunity to compare those measurements with the corresponding measurements obtained for adults and older children who are capable of performing the maneuver voluntarily under instructions.

The invention also comprises an apparatus for performing the maximum forced expiration in infants under automatic control which apparatus comprises inflation means for inflating the lungs of the infant with air to a volume greater than that attained at end-tidal inspiration;

means for sensing the air flow of the infant's inspiration and expiration and sending a flow rate signal to a controller;

means for sensing the air pressure in the infant's lungs and sending an air pressure signal to the controller;

compression means to compress the lungs of the infant by compressing the infant's chest and/or abdomen to perform a forced expiration;

controller means for receiving the air flow signal and the air pressure signal, determining from those signals the infant's natural inspirations, commanding the inflation means to first inflate the infant's lungs synchronously with normal tidal inspiration until the infant's breathing pauses, determining from the air flow and air pressure signals the pause in the infant's breathing, commanding the inflation means to inflate the infant's lungs to substantially total lung capacity, determining from the air flow and air pressure signals the completion of the inflation to total lung capacity, commanding the compression means to compress the infant's thoracoabdominal region to produce a maximum forced expiration, determining from the air flow and air pressure signals the termination of the forced expiration and commanding the compression means to cease compression.

Accordingly, it is an object of the invention to provide a method of producing a maximum forced flow vital capacity expiratory maneuver in infants.

A further object is to provide a method for generating forced flow volume curves representative of pulmonary function in infants.

A further object is to provide a method for determining forced vital capacity in infants.

A further object is to provide apparatus for determining forced flow volume curves in infants.

A further object is to provide a method for obtaining adult-type lung function data in infants.

A further object is to provide a method for the determination of fractional lung volumes in infants.

A further object is to provide apparatus for obtaining forced flow volume curves representative of pulmonary function in infants.

Other objects of the invention will become apparent from the description of the invention which follows.

DETAILED DESCRIPTION OF THE INVENTION AND PREFERRED EMBODIMENTS

The goal of the method of this invention and the apparatus for carrying out that method under automatic control is to provide a forced expiratory maneuver over the entire vital capacity range in infants to provide the data for calculating fractional lung volumes (FLVs) and plotting full flow-volume curves (FFVCs) for infants which are comparable to the corresponding measurements obtainable for older children and adults.

Figure 1:
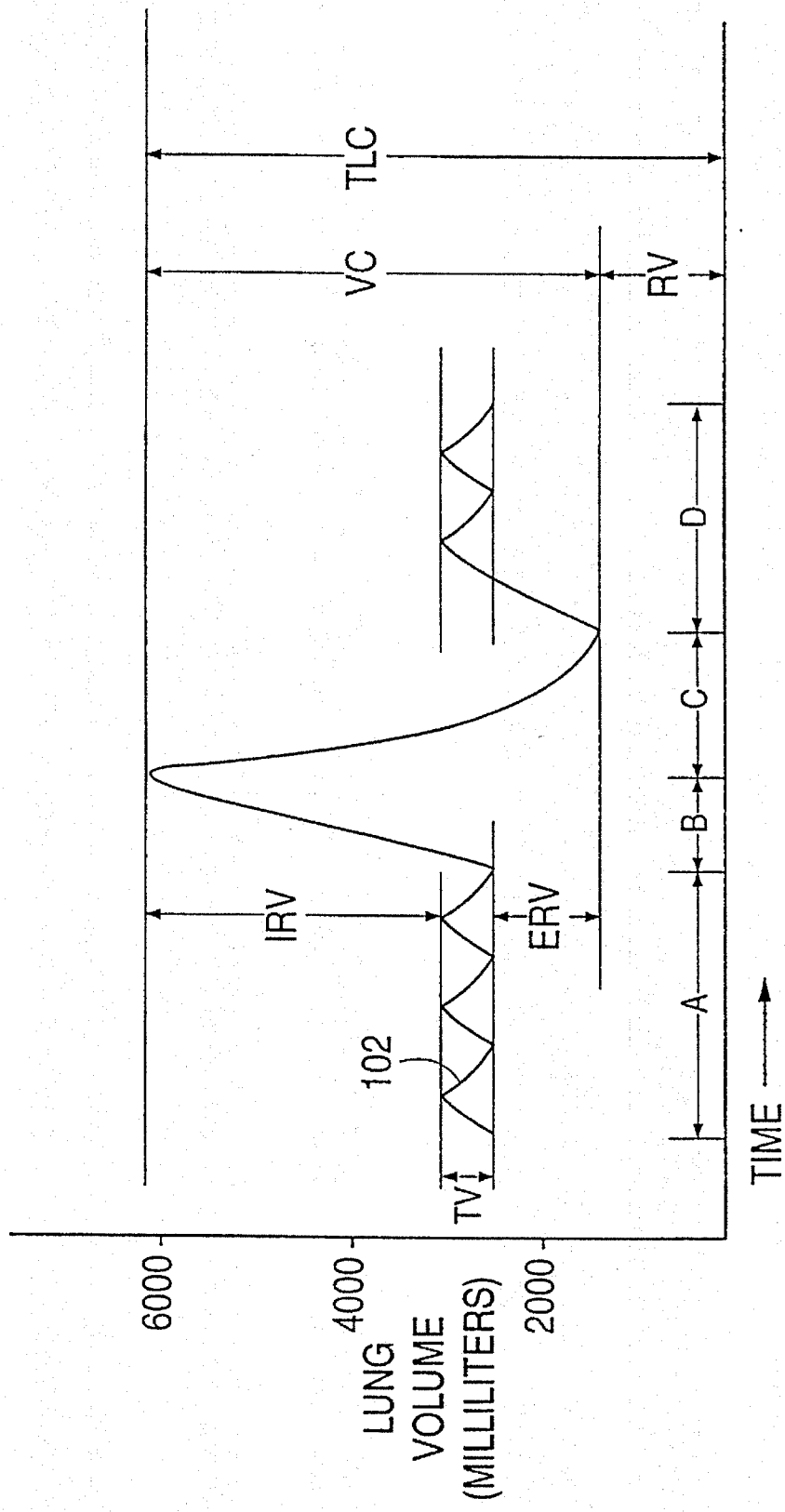
FIG. 1 is a schematic plot of the respiratory volume versus time associated with a forced vital capacity maneuver in adults, showing the fractional lung volumes that are of interest in evaluating pulmonary function.

The pattern of breathing prescribed for an adult maximum forced expiratory flow maneuver test is schematically illustrated in FIG. 1. The vertical axis in the plot of FIG. 1 represents lung volume and is scaled for an average adult lung capacity. Of the total lung capacity (TLC), a portion, the residual volume (RV), can not be emptied of air by even a maximum exhalation. The portion of the lung volume that can be exchanged by maximum inhalation and expiration is known as the vital capacity (VC). The horizontal axis represents time, and the trace 102 represents the amount of air contained in the lung at a given time. The portion of the plot indicated as A represents normal tidal breathing, which uses a relatively small proportion of the total lung volume, defined as tidal volume (TV), leaving substantial volumes available for maximum inspiration (the inspiratory reserve volume, IRV) and maximum expiration (the expiratory reserve volume, ERV). The pattern of tidal breathing shown indicates a regular inspiration and expiration without pause, but, in practice, adults at rest often pause briefly between breaths for short periods of time. At the beginning of the forced vital capacity maneuver, the subject makes a maximum inspiration effort to fill the lungs to maximum capacity, indicated at B on the plot. The subject then immediately exhales as forcefully as possible to exhale as much of the air from the lungs as possible, shown at C in FIG. 1. After the forced expiration the subject returns to tidal breathing at D.

It can readily be seen from FIG. 1 that under various conditions of breathing, different proportions of the total lung volume are used. The fraction of the total lung volume that can be exhaled in the maximum forced expiration is generally known as the vital capacity (VC). The time that an individual requires to perform the maximum forced expiration can also be used to provide useful diagnostic indices. For example the volume that can be exhaled in one second (forced expiratory volume—one second, $FEV_1$) and the expiratory flow rate averaged over the period from a volume of 25% to 75% of the total expired air volume ($FEV_{25-75}$) are useful in evaluating pulmonary function.

Figure 2:
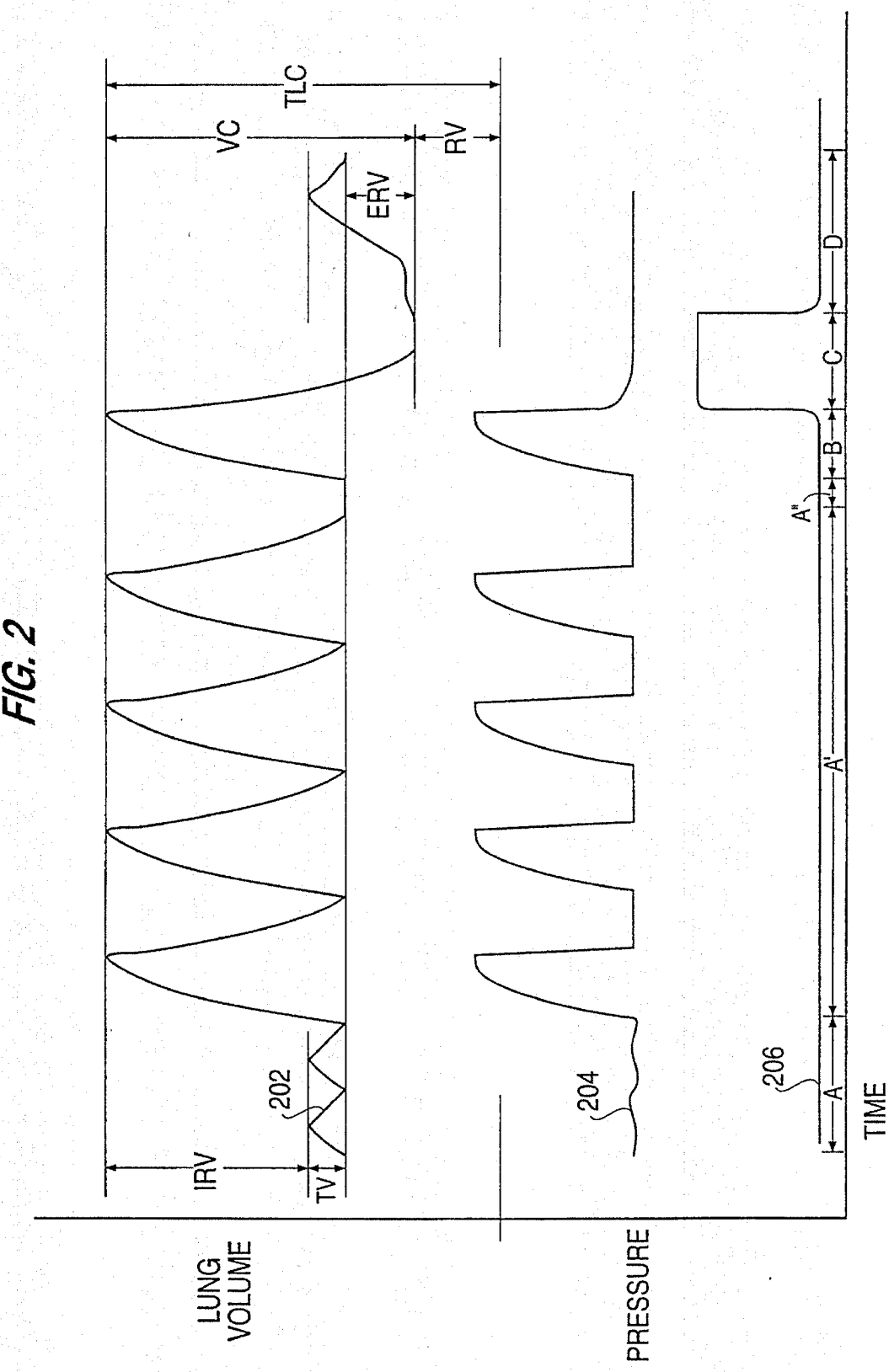
FIG. 2 is a plot showing the respiratory volume versus time for an infant undergoing the procedure of this invention.

In order to provide flow-volume data over fractional lung volumes comparable to those obtained in adults, the method of the invention has been devised. FIG. 2 is a spirogram illustrating the breathing pattern produced in an infant by the method of the invention, wherein the relevant events are indicated as functions of time by three traces. In FIG. 2 the breathing pattern is represented by trace 202, while the portion of the vertical axis adjacent trace 202 represents relative lung volume, because the absolute volumes of the infants may vary widely. Trace 204 represents the air pressure applied at the mouth of the infant to inflate the lungs to a substantially greater volume, while trace 206 represents the pressure compressing the thoracic vest used to provide rapid forced expiration of the inspired air. The vertical axis adjacent to traces 204 and 206 represents relative pressure.

Because infants breath continuously under positive control, inspiration and expiration follow one another continuously in a tidal cycle as shown at A in FIG. 2. Occasionally, an infant will pause in breathing, usually after taking an unusually deep breath and exhaling it in a kind of sigh. In order to produce such a pause under controlled laboratory conditions, the infant is artificially inflated with air through a face mask synchronously with its natural inspiration to simulate natural deep breathing. The only practical circumstances under which infants will tolerate this artificial inspiration is when they are asleep. In some cases, particularly with very young infants, it is possible do perform the maneuver during natural sleep. However, in almost all cases it is necessary to sedate the infant in order to place it into a state of sleep wherein it will tolerate the application of a face mask. When the infant has been suitable sedated, a face mask having a controllable air supply is placed over the infant's nose and mouth. The mask must make a relatively tight seal to the infant's face to prevent leakage of air at the edges. A mask with a suitable soft sealing edge may be used. However, it has been found that the face mask may be very effectively and conveniently sealed by pressing it gently against the infant's face and sealing the edge with medical putty, which provides a good air seal and is easily removed after the procedure has been completed. A flow measuring device, e.g., a pneumotachograph is placed in the air inlet conduit to the mask to provide a measure of the airflow in and out of the infant's lungs for determining the flow rates and lung volumes, and to provide a control signal when the method is performed under automatic control. The infant is also provided with a device to produce thoracoabdominal compression in order to produce a forced expiration. Typically an inflatable vest is used which compresses the infant's thoracoabdominal region to produce a forced expiration. The infant is then allowed to breathe tidally as indicated at A in FIG. 2. In order to reduce resting levels of $CO_2$ and produce a controlled respiratory pause the infant is inflated with extra air synchronously with its natural breathing rhythm. This is accomplished by applying a superatmospheric air pressure of about 30 cm of water to the face mask, as shown in trace 204 of FIG. 2. The corresponding increase in breathing is shown by trace 202 in region A', which shows substantially maximum inspirations followed by natural expirations to the functional residual capacity (FRC) as is usual in tidal respiration. After a number of breathing cycles, which may vary from 1 to 15, the infant will pause in its breathing as shown at A" in FIG. 2. When the infant pauses in breathing, its lungs are promptly inflated to substantially maximum capacity by application of air pressure through the mask, as shown in region B of trace 202. The pause at A" is shown, for illustrative purposes, as lasting for a definite time. However, in practice, it is preferred to initiate the forced inspiration as soon as possible after the beginning of the pause. Inasmuch as the pause in the infant's breathing is readily detected, the actual time between the beginning of the pause A" and the initiation of the forced inspiration B is usually very short, i.e., substantially less than one second. Typically, the forced inspiration is carried out at a pressure of about 30 cm of water. As soon as the infant's lungs have been inflated, the thoracoabdominal vest is inflated as shown at region C of trace 206 in FIG. 2. The corresponding simultaneous expiration is shown by trace 202. The total length of the pause in active respiratory effort may last from 2 to 5 seconds, which is ample time to perform the forced expiratory maneuver of the invention. The pressure in the inflatable vest is adjusted to produce a maximum expiration. The proper pressure can be determined by repeating the maneuver at increasing vest pressures until forced expiratory flows over most of the vital capacity range reach an upper limit or maximum. Typically the pressure used in the inflatable vest will range from about 40 cm of water to about 100 cm of water, preferably 60 cm of water to 80 cm of water.

When the forced expiratory maneuver is complete, as indicated by the cessation of outflow, e.g., as measured by the pneumotachograph, the vest pressure is immediately released, as shown in trace 206, and the infant returns to normal tidal breathing as shown by trace 202 in region D in FIG. 2. Typically, normal tidal breathing is reestablished in 5 to 15 breaths.

The signal output of the pneumotachograph is an air flow rate that may be used as one input in the preparation of a flow-volume curve, and is integrated to give the volumes inhaled and exhaled by the infant during the maneuver. Because the flow-volume curves obtained by this method in infants are closely analogous to maximum forced expiratory measurements obtained in older children and adults, they can be more easily interpreted and used for diagnosis and prognosis of lung disease in infants.

Figure 3:
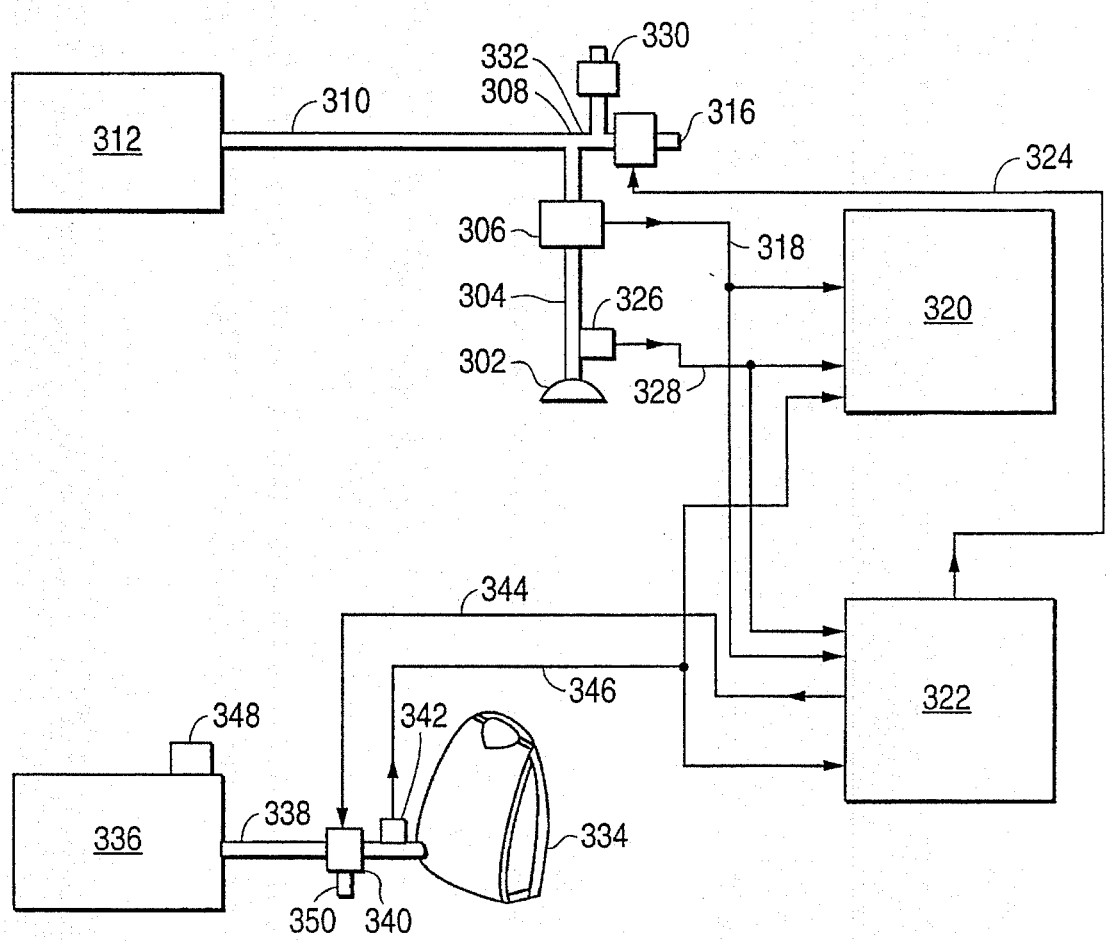
FIG. 3 is a schematic diagram of an embodiment of an apparatus used in practicing the method of this invention.

An apparatus suitable for practicing the method of the invention under automatic control is illustrated in FIG. 3.

A face mask 302 adapted to be fitted over the infant's nose and mouth and sealed thereto with medical putty is connected via mask air conduit 304 and pneumotachograph 306 to a T-fitting 308 in a breathable air supply line 310. The air supply line 310 is connected to a source of breathable air 312 capable of providing a pressure at the infant's mouth sufficient for inflation of the infant's lungs to full capacity. In practice, a pressure of about 30 cm of water is adequate. It will be recognized by those skilled in the art that the internal volume of the air conduits and other apparatus between the air supply conduit 310 and the infant's nose and mouth within the mask 302 should be as small as possible to reduce the dead volume, i.e., the air rebreathed by the infant, to as small a value as possible. Consequently the arrangement in FIG. 3 is to be interpreted as schematic only, for purposes of showing the connection and operation of the parts of the apparatus. In practice, the air conduit 304 and the connection between the pneumotachograph 306 and the air supply conduit 310 are made as short as possible, and the pneumotachograph 306 and mask 302 are constructed to have the minimum possible internal volume, consistent with free flow of air to and from the infant.

In order to compress the infant's lungs to produce the forced expiratory maneuver, the infant is fitted with an inflatable vest 334 which, when inflated, compresses the infant's thoracoabdominal region. Such vests are available in several designs, and any vest or other thoracoabdominal compression device that is capable of producing a forced expiration to residual lung volume is suitable. Such devices are typically pneumatically operated, but devices that provide equivalent function, whether operated electrically, hydraulically or mechanically or the like, are also suitable for the apparatus of the invention. In the illustrated embodiment the pneumatic vest 334 is connected to a source of pressurized gas 336 through a pressurized gas conduit 338 provided with a vest inflation valve 340 and a vest pressure sensor 342. The gas pressure provided by the source of pressurized gas 336 may be adjusted by a pressure controller, illustrated schematically as 344.

At the beginning of the procedure of the invention for performing a forced expiratory maneuver, air flows from the source 312, through the supply line 310, the cross-arm of the T-fitting 308, the exhaust arm 332 of the apparatus, and the breath control 314 and is exhausted to the atmosphere through exhaust port 316. Together the air supply conduit 310, T-fitting 308, exhaust arm 332, breath control valve 314, pressure limit valve 330, and exhaust port 316 constitute a manifold for distribution and control of the breathable air. With the air freely flowing through this manifold, the infant can perform natural tidal respiration without restriction by inhaling and exhaling through the pneumotachograph 306 and mask air conduit 304. The pneumotachograph 306 measures the inflow and outflow of air as the infant breathes and provides a signal through pneumotachograph signal line 318 to the data recorder 320 and the controller 322. In order to inflate the lungs of the infant synchronously with its inspiration, the controller operates the apparatus as follows. When the pneumotachograph signal transmitted over pneumotachograph signal line 318 indicates the beginning of an inspiration, the controller 322 transmits a control signal over breath control valve control line 326 commanding the breath control valve 324 to close. When the breath control valve 324 is closed, the air from the breathable air supply 312 is directed into the infant's lungs. The pressure within the mask, i.e., the infant's mouth pressure, is monitored by the mouth pressure sensor 328 located in the mask conduit 304. Alternatively, the mouth pressure sensor could be located in the mask itself or anywhere in the air supply conduit system close enough to the mask to provide a pressure reading equivalent to the pressure at the infant's mouth. A pressure limit valve 330 (popoff valve) opens when the pressure reaches a preset value. The pressure limit valve 330 is shown as located in the exhaust arm 332 of the air supply manifold. However, like the mouth pressure sensor 328, the pressure limit valve 330 can be located anywhere within the air supply system close enough to the face mask to provide effective limitation of the pressure applied to the infant's lungs (the mouth pressure). The maximum pressure to which the infant's lungs are inflated is controlled by setting the pressure at which the pressure limit valve 330 opens. Typically, a pressure of about 30 cm of water is selected. After each inspiration, when the pressure reaches a preset level, the air exhaust valve 314 is opened on command of the controller 322 transmitted over breath control valve control line 324, and the infant exhales freely.

After several enhanced inspirations, the infant will pause in breathing, as discussed above. When the pause is detected by an indication from the pneumotachograph that no air is flowing into or out of the infant's lungs, the controller 322 commands the closure of the air exhaust valve 314, and the infant's lungs are again inflated to a pressure of about 30 cm of water. As soon as the inflation is complete, the controller 322 opens the air exhaust valve 314 and commands the vest inflation valve 340 via the vest inflation valve control line 344 to switch to the inflation position to inflate the vest 334 to a preselected pressure. The vest pressure is monitored by the vest pressure sensor 342 which transmits a signal via the vest pressure sensor signal line 346 to the controller and the data recorder. When a study is begun on a particular infant patient, the vest inflation pressure is initially adjusted by gas pressure control 348 to a relatively low value, e.g., about 40 cm of water. Subsequently, the procedure is repeated using incrementally higher pressures until a maximum forced expiration is reached, indicating that the lung volume has been reduced to residual volume and the forced expiration is an adequate measure of the infant's vital capacity. Once the forced expiratory maneuver is complete, as indicated by the termination of expiratory flow through the pneumotachograph 306, the controller 322 commands the vest inflation valve 344 to switch to its exhaust position, connecting the vest 334 to the vest exhaust port 350, thereby deflating the vest 334 and allowing the infant to resume normal tidal breathing.

The flow rates of air in an out of the infant's lungs is recorded by the data recorder 320, and the data so collected can be used to derive standard measures of pulmonary function such as the vital capacity, various measures of forced expiration rate, and the like. The $FEV_{25-75}$ and other flows at specific lung volume levels are generally more useful in infants than the $FEV_1$ because the forced expiration is often completed in less than one second in infants.

It will be understood that the embodiment of the apparatus described above is only one apparatus suitable for carrying out the process of this invention. Various modifications are possible, For example, the controller 322 and data recorder 320 are shown as separate units. Either or both of these units could be an appropriately programmed digital computer or, in a preferred embodiment, the functions of both units could be performed by a single appropriately programmed digital computer. The data and control signal lines may be direct electrical connections or may be fiber optic cables or even radio or infrared radiation signalling data links as is well known to those skilled in the art. Any appropriate means may be used to sense and quantitate the airflow into and out of the infant's lungs. The actual volume of the air could be measured by an appropriate spirometer instead of being calculated by integrating the flow rate signal from the pneumotachograph. It will also be understood by those skilled in the art that the mask may be constructed differently to perform its function. For example, separate passages could be provided for inhaled air and exhaled air, with the breath control valve being located in exhaust passage and appropriate flow-measuring devices in each passage.

The above-described apparatus for performing the process of the invention incorporates a controller means which receives signals from various sensors and outputs control signals to operate the various valves in the apparatus. It will be recognized by those skilled in the art that the process can be performed manually by a skilled practitioner using the forced respiration means and the forced expiration means of the apparatus. In the manual operation procedure the skilled practitioner would observe the signals from the sensing devices as recorded and displayed by the recording device 320 and actuate the exhaust valve 316 and the vest inflation valve 340 at the appropriate times to produce the maximum forced expiration maneuver in the infant. The data from the performance of the maneuver would be recorded and processed by the recorder 320 in the same way as during automatic operation.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

I claim:

1. A method for performing a forced expiratory maneuver in an infant comprising the steps of 1.) inflating the lungs of an infant with air synchronously with natural tidal inspiration to a lung volume greater than that reached at end tidal inspiration for a plurality of consecutive respiratory cycles until the infant's natural tidal breathing pauses;

2.) during said pause in breathing, rapidly inflating the infant's lungs to substantially total lung volume; and 3.) immediately compressing the chest and abdomen of said infant to produce a maximum forced expiration.

2. The method of claim 1 additionally comprising sedating said infant before step 1.) is performed.

3. The method of claim 1 comprising inflating the lungs of said infant in step 1) synchronously with said natural tidal inspiration to a pressure of about 30 cm of water.

4. The method of claim 1 comprising inflating the lungs of said infant in step 2.) to a pressure of about 30 cm of water.

5. The method of claim 1 wherein said compression in step 3 is performed by compressing said chest and abdomen with an inflatable vest.

6. The method of claim 5 comprising inflating said inflatable vest to a pressure of about 40 cm of water to about 100 cm of water.

7. An apparatus for performing a maximum forced expiration maneuver in infants comprising control means, inflation means, responsive to said control means, for inflating the lungs of an infant with air to a volume greater than that reached at end-tidal inspiration in said infant's natural respiration, means for sensing a rate of airflow of said infant's respiration and sending a flow rate signal representative of said rate of airflow to said control means, means for sensing the pressure of said air inflating the lungs of said infant and sending an inflation pressure signal representative of said inflation pressure to said control means, compression means, responsive to said control means, for compressing the lungs of said infant, said control means being responsive to said flow rate signal and said inflation pressure signal whereby said control means 1.) commands said inflation means to inflate said lungs of said infant synchronously with said infant's natural inspiration, 2.) detects a pause in said infant's natural respiration, 3.) thereupon commands said inflation means to inflate said infant's lungs to substantially total lung volume, and 4.) commands said compression means to compress said infant's lungs to substantially residual volume.

8. The apparatus of claim 7 wherein said inflation means comprises a source of breathable air at superatmospheric pressure, a face mask, a conduit for carrying said air at superatmospheric pressure from said source to said face mask, and valve means for directing said air at superatmospheric pressure into said infant's lungs on command of said control means.

9. The apparatus of claim 8 wherein said valve means comprises an exhaust valve in fluid communication with said conduit, said exhaust valve having an open position wherein said exhaust valve permits said air at superatmospheric pressure to escape from said conduit and a closed position wherein said exhaust valve prevents said air from escaping from said conduit thereby directing said air into said infant's lungs.

10. The apparatus of claim 8 additionally comprising a pressure limit valve for venting said air in said conduit when said superatmospheric pressure of said air exceeds a predetermined value.

11. The apparatus of claim 7 wherein said means for sensing airflow rate is a pneumotachograph.

12. The apparatus of claim 7 wherein said compression means comprises an inflatable vest, a source of pressurized gas, a conduit for conducting said gas from said source to said vest, and a vest inflation valve means for connecting said vest to said source of pressurized gas or to a vent.

13. The apparatus of claim 12 additionally comprising means for sensing pressure of said gas in said vest and sending a vest pressure signal to said control means.

14. The apparatus of claim 7 wherein said control means comprises means for detecting said infant's natural inspirations, means for commanding said inflation means to inflate said infant's lungs synchronously with said natural inspirations for a series of inspirations, means for detecting a pause in said infant's respiration, means for commanding said inflation means to inflate said infant's lungs to substantially total lung volume, and means for commanding said compression means to compress said infant's lungs to substantially residual volume.

15. The apparatus of claim 7 additionally comprising data recording means for receiving and recording at least one of said flow rate signal, said inflation pressure signal and said vest pressure signal.

16. An apparatus for performing a maximum forced expiration an infant comprising a) a source of breathable air at superatmospheric pressure, b) an air distribution manifold in fluid communication with said source of air, c) a pneumotachograph in fluid communication with said manifold, d) a face mask in fluid communication with said pneumotachograph, e) an exhaust port in fluid communication with said manifold, f) an exhaust valve capable of opening and closing said exhaust port under command of a controller, g) a mouth air pressure sensor in fluid communication with said face mask, h) a pressure limit valve in fluid communication with said manifold, i) an inflatable vest for said infant, j) a source of pressurized gas, k) a pressurized gas conduit in fluid communication with said source of pressurized gas and said inflatable vest, l) a two-position vest inflation valve in said pressurized gas conduit capable of, in a first position, connecting said vest to said source of pressurized gas and, in a second position, connecting said vest to a vest exhaust port, m) a vest pressure sensor in fluid communication with said inflatable vest, n) an electronic controller capable of receiving signals from said pneumotachograph, said mouth pressure sensor and said vest pressure sensor 1.) commanding said inflation means to inflate said lungs of said infant synchronously with said infant's natural inspiration, 2.) detecting a pause in said infant's natural respiration, 3.) thereupon commanding said inflation means to inflate said infant's lungs to substantially total lung volume, and 4.) commanding said compression means to compress said infant's lungs to substantially residual volume.

17. The apparatus of claim 16 additionally comprising o) a data recorder receiving signals from said pneumotachograph and said mouth pressure sensor.

* * * * *

UNITED STATES PATENT AND TRADEMARK OFFICE
CERTIFICATE OF CORRECTION

PATENT NO. : 5,513,647

DATED : May 7, 1996

INVENTOR(S) : Robert G. Castile

It is certified that error appears in the above-identified patent and that said Letters Patent is hereby corrected as shown below:

On the title page item [73], insert --Children's Hospital, Inc., Columbus, Ohio--.

Signed and Sealed this

Eighth Day of October, 1996

Attest:

BRUCE LEHMAN

Attesting Officer

Commissioner of Patents and Trademarks